United States Patent
Thenappan et al.

(10) Patent No.: US 6,689,924 B1
(45) Date of Patent: Feb. 10, 2004

(54) LIQUID PHASE CATALYTIC FLUORINATION OF HYDROCHLOROCARBON AND HYDROCHLOROFLUOROCARBON

(75) Inventors: Alagappan Thenappan, Cheektowaga, NY (US); Hsueh S. Tung, Getzville, NY (US); Robert L. Bell, Amherst, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 09/467,869

(22) Filed: Dec. 20, 1999

Related U.S. Application Data

(62) Division of application No. 08/744,157, filed on Nov. 12, 1996, now Pat. No. 6,023,004.

(51) Int. Cl.$^7$ .............................................. C07C 17/00
(52) U.S. Cl. ........................ 570/167; 526/906; 526/913
(58) Field of Search ........................................ 570/167

(56) References Cited

U.S. PATENT DOCUMENTS

| | | | |
|---|---|---|---|
| 2,942,036 A | 6/1960 | Smith et al. ................ | 260/653 |
| 4,138,355 A | 2/1979 | Ferstandig .................. | 252/182 |
| 4,258,225 A | 3/1981 | Feiring ....................... | 570/168 |
| 5,496,866 A | 3/1996 | Sommerfeld et al. ....... | 521/131 |
| 5,574,192 A | * 11/1996 | Van Der Puy et al. ..... | 570/167 |

FOREIGN PATENT DOCUMENTS

| | | |
|---|---|---|
| EP | 0 381 586 A1 | 8/1990 |
| EP | 0 405 615 B1 | 1/1991 |
| EP | 0 611 744 A1 | 8/1994 |
| EP | 0703205 A1 | 3/1996 |
| JP | 272086 | 11/1990 |
| JP | 6-263659 | 9/1994 |
| WO | WO 94/29251 | 12/1994 |
| WO | WO 95/04022 | 2/1995 |

OTHER PUBLICATIONS

Boutevin et al., 97:182966c , Synthetic High Polymers, vol. 97, p. 7, (1982).
Feiring, Chemistry in Hydrogen Fluoride V. Catalysts for Reaction of HF with Halogenated Olefins, Journal of Fluorine Chemistry, vol. 13, pp. 7–18, (1979).
Wendlinger et al., 124:342631w , CA Selects. Organofluorine Chemistry, Issue 13, p. 7 (1996).
Kotora et al., Selective Additions of Polyhalogenated Compounds to Chlorosubstituted Ethenes Catalyzed by a Copper Complex, React. Kinet. Catal. Lett., vol. 44, No. 2, 415–419 (1991).

* cited by examiner

Primary Examiner—Johann Richter
Assistant Examiner—Karl Puttlitz
(74) Attorney, Agent, or Firm—Colleen D. Szuch

(57) ABSTRACT

A process for the catalytic fluorination of hydrochlorocarbons and hydrochlorofluorocarbons in the liquid phase. The process is useful for fluorinating hydrochloropropanes, hydrochlorofluoropropanes, hydrochloropropenes and hydrochlorofluoropropenes and most particularly useful for fluorinating 1,1,1,3,3-pentachloropropane to 1,1,1,3,3-pentafloropropane. Suitable catalysts include (i) a pentavalent molybdenum halide; (ii) a tetravalent tin halide; (iii) a tetravalent titanium halide; (iv) a mixture of a pentavalent tantalum halide with a tetravalent tin halide; (v) a mixture of a pentavalent tantalum halide with a tetravalent titanium halide; (vi) a mixture of a pentavalent niobium halide with a tetravalent tin halide; (vii) a mixture of a pentavalent niobium halide with a tetravalent titanium halide; (viii) a mixture of a pentavalent antimony halide with a tetravalent tin halide; (ix) a mixture of a pentavalent antimony halide with a tetravalent titanium halide; (x) a mixture of a pentavalent molybdenum halide with a tetravalent tin halide; (xi) a mixture of a pentavalent molybdenum halide with a tetravalent titanium halide and (xii) a mixture of a pentavalent antimony halide with a trivalent antimony halide. Products of this process are useful in a variety of applications including solvents, blowing agents, and refrigerants.

32 Claims, No Drawings

LIQUID PHASE CATALYTIC FLUORINATION OF HYDROCHLOROCARBON AND HYDROCHLOROFLUOROCARBON

This application is a division of U.S. patent application Ser. No. 08/744,157 filed Nov. 12, 1996, now U.S. Pat. No. 6,023,004, issued Feb. 8, 2000.

BACKGROUND OF THE INVENTION

1. Field of the Invention

The present invention relates to the fluorination of hydrochlorocarbons and hydrochlorofluorocarbons. More particularly, the invention pertains to the catalytic fluorination of hydrochlorocarbons and hydrochlorofluorocarbons in the liquid phase. The process is useful for fluorinating hydrochloropropanes, hydrochlorofluoropropanes, hydrochloropropenes and hydrochlorofluoropropenes and most particularly useful for fluorinating 1,1,1,3,3-pentachloropropane to 1,1,1,3,3-pentafluoropropane.

2. Description of the Prior Art

In recent years there has been universal concern that completely halogenated chlorofluorocarbons (CFCs) might be detrimental to the Earth's ozone layer. Consequently, there is a worldwide effort to use fluorine-substituted hydrocarbons which contain fewer or no chlorine substituents.

Hydrofluorocarbons (HFCs) are of great interest due to their potential to replace ozone depleting CFCs and hydrochlorofluorocarbons (HCFCs) in a variety of applications such as solvents, blowing agents, refrigerants, cleaning agents, aerosol propellants, heat transfer media, dielectrics, fire extinguishing compositions and power cycle working fluids. It is known in the art to produce fluorocarbons such as HFCs by reacting hydrogen fluoride with various hydrochlorocarbon compounds. In this regard, 1,1,1,3,3-pentafluoropropane (HFC-245fa), a hydrofluorocarbon having zero ozone depletion potential, is being considered as a replacement for CFCs such as dichlorodifluoromethane in refrigeration systems and trichlorofluoromethane as a blowing agent. See U.S. Pat. No. 2,942,036, Canadian 684,687, EP 381 986A, JP 02,272,086, WO 95/04022, U.S. Pat. No. 5,496,866 (foam blowing agent) and European Patent No. 2,942,036 (aerosol propellant).

Methods to produce HFC-245fa are also known in the art. See, e.g. WO 95/04022 (reaction of 3-chloro-1,1,1 3,3-pentafluoropropane with hydrogen over a reduction catalyst); WO 94/29,251 (hydrogenation of 1,1,3,3,3-pentafluoropropene with hydrogen in the gas phase at 40–300° C. using a palladium catalyst; European Patent 611,744 (hydrogenation of di- or trichloropropanes); U.S. patent application Ser. No. 08/519,857, filed Aug. 25, 1995 (reaction of carbon tetrachloride with vinyl chloride to give $CCl_3CH_2CHCl_2$ (HCC-240fa) followed by fluorination with HF in the presence of a fluorination catalyst including pentavalent antimony, niobium, arsenic and tantalum halides and mixed halides. However, these methods are not without their shortcomings. For example, hydrogenation of mono-, di- or tri-chloropentafluoropropanes and unsaturated pentafluoropropene has several disadvantages, namely, multiple steps necessary for the preparation of the feed materials, a higher reaction temperature and poor selectivity to the desired product. Fluorination of HCC-240fa with HF in the presence of a pentavalent antimony halide catalyst shows a high corrosion rate when a metallic reactor is used. See U.S. Pat. No. 4,138,355.

Also known in the art are reactions of unsaturated, halogenated olefins such as tri- and tetrachloroethenes with HF in the presence of tantalum pentafluoride, niobium pentafluoride, molybdenum pentachloride, and titanium tetrachloride. See Feiring, A. E. in Journal of Fluorine Chemistry, 14, 7(1979); U.S. Pat. No. 4,258,225 (tantalum pentafluoride and niobium pentafluoride as liquid phase catalysts).

Other known fluorination catalysts include tin salts or organotin compounds along with oxygen-containing compounds, see European Patent Application 187,643 (production of 1,1-dichloro-1-fluoroethane, HCFC-141b), tin tetrachloride, see U.S.S.R. Patent 341,788 (liquid-phase process to produce 1,1-difluoroethane, HFC-152a from vinyl chloride), and mixtures of pentavalent and trivalent antimony halides, U.S. Pat. No. 4,138,355 (production of $CF_3CH_2CH_2Cl$, HCFC-153fb, from 1,1,1,3-tetrachloropropane, $CCl_3CH_2CH_2Cl$, HCC-250fb). All of the foregoing patents and application are incorporated herein by reference.

It would be advantageous to achieve the catalytic fluorination of HCCs and HCFCs with HF under less corrosive conditions using metal reactors. The use of tetravalent tin or titanium halide or an equal molar mixture of trivalent and pentavalent antimony halides or molybdenum pentahalide as a fluorination catalyst to fluorinate polychlorinated compounds with a $—CHF_yCl_{2-y}$, wherein y=0 or 1 end group to give polyfluorinated compounds with a $—CHF_2$ terminal group is not known in the art. In particular, fluorination of HCC-240fa with HF to form HFC-245fa in the presence of tin, titanium, molybdenum or mixture of antimony(V) and antimony(III) halides is not known in the art.

SUMMARY OF THE INVENTION

The invention provides a fluorinating process which comprises reacting at least one hydrochlorocarbon or hydrochlorofluorocarbon compound with hydrogen fluoride in the liquid phase and in the presence of at least one catalyst selected from the group consisting of (i) a pentavalent molybdenum halide of the formula $MoCl_{5-z}F_z$ wherein z is 0 to 5; (ii) a tetravalent tin halide of the formula $SnCl_{4-y}F_y$ wherein y is 0 to 4; (iii) a tetravalent titanium halide of the formula $TiCl_{4-x}F_x$ wherein x is 0 to 4; (iv) mixtures of a pentavalent tantalum halide of the formula $TaCl_{5-n}F_n$ wherein n is 0 to 5 with a tetravalent tin halide of the formula $SnCl_{4-y}F_y$ wherein y is 0 to 4; (v) mixtures of a pentavalent tantalum halide of the formula $TaCl_{5-n}F_n$ wherein n is 0 to 5 with a tetravalent titanium halide of the formula $TiCl_{4-x}F_x$ wherein x is 0 to 4; (vi) mixtures of a pentavalent niobium halide of the formula $NbCl_{5-m}F_m$ wherein m is 0 to 5 with a tetravalent tin halide of the formula $SnCl_{4-y}F_y$ wherein y is 0 to 4; (vii) mixtures of a pentavalent niobium halide of the formula $NbCl_{5-m}F_m$ wherein m is 0 to 5 with a tetravalent titanium halide of the formula $TiCl_{4-x}F_x$ wherein x is 0 to 4; (viii) mixtures of a pentavalent antimony halide of the formula $SbCl_{5-p}F_p$ wherein p is 0 to 5 with a tetravalent tin halide of the formula $SnCl_{4-y}F_y$ wherein y is 0 to 4; (ix) mixtures of a pentavalent antimony halide of the formula $SbCl_{5-p}F_p$ wherein p is 0 to 5 with a tetravalent titanium halide of the formula $TiCl_{4-x}F_x$ wherein x is 0 to 4; (x) mixtures of a pentavalent molybdenum halide of the formula $MoCl_{5-z}F_z$ wherein z is 0 to 5 with a tetravalent tin halide of the formula $SnCl_{4-y}F_y$ wherein y is 0 to 4; (xi) mixtures of a pentavalent molybdenum halide of the formula $MoCl_{5-z}F_z$ wherein z is 0 to 5 with a tetravalent titanium halide of the formula $TiCl_{4-x}F_x$ wherein x is 0 to 4 and (xii) mixtures of a pentavalent antimony halide of the formula $SbCl_{5-p}F_p$ wherein p is 0 to 5 with a trivalent antimony halide of the formula $SbCl_{3-p}F_p$ wherein p is 0 to 3.

The process of this invention achieves fluorination of HFCs and HCFCs under less corrosive conditions than prior art processes.

DETAILED DESCRIPTION OF THE PREFERRED EMBODIMENT

The invention concerns the catalytic fluorination of HCCs and HCFCs in the liquid phase with hydrogen fluoride. In the practice of the present invention, a liquid phase catalyst as described below is charged into a fluorination reactor prior to heating the reactor. The reactor according to this invention may preferably be any suitable fluorination reaction pressure vessel or autoclave but preferably may be constructed from materials which are resistant to the corrosive effects of HF such as Hastelloy-C, Inconel, Monel and fluoropolymer-lined vessels. Such liquid phase fluorination reactors are well known in the art. Then the HF and the HCC or HCFC compound to be fluorinated and HF are fed to the reactor after the reactor reaches the desired temperature.

In the preferred embodiment, the reaction is conducted at a temperature of from about 50° C. to about 200° C., more preferably from about 90° C. to about 140° C. In the preferred embodiment, the reaction is conducted for from about 1 to about 25 hours, more preferably from about 2 to about 8 hours. The pressure of the reaction is not critical and it varies depending on the quantity of hydrogen fluoride used, hydrogen chloride generated and conversion of organics. Convenient operating pressure ranges from about 50 to about 600 psig, and preferably from 50–400 psig. Pressure may be adjusted by continuously removing hydrogen chloride and volatile products from the reactor by distillation.

In the preferred embodiment, the catalyst is present in an amount, based on the mole percent of HCC or HCFC or mixtures thereof of from about 2% to about 80%, and preferably from about 5% to about 50%, and most preferably from about 10% to about 20%. Fluorination catalysts having a purity of at least 98% are preferred.

Based on reaction stoichiometry, the required mole ratio of HF to organics (i.e. HFCs and HCFCs) is at least equal to the number of chlorine atoms to be replaced in the starting organic material and preferably is relatively in an excess. In the preferred embodiment, the mole ratio of HF to HCC or HCFC compound ranges from at least about 1:1, more preferably from about 1:1 to about 15:1 and most preferably from about 6:1 to about 15:1.

Any water in the HF will react with and deactivate the catalyst. Therefore substantially anhydrous HF is preferred. By "substantially anhydrous" we mean that the HF contains less than about 0.05 weight % water and preferably contains less than about 0.02 weight % water. However, one of ordinary skill in the art will appreciate that the presence of water in the catalyst can be compensated for by increasing the amount of catalyst used. HF suitable for use in the reaction may be purchased from AlliedSignal Inc. of Morristown, N.J.

In the preferred embodiment, the HCC or HCFC compound useful for the invention includes hydrochloroalkanes and hydrochlorofluoroalkanes having the formula $CF_xCl_{3-x}CH_2CHF_yCl_{2-y}$, wherein x is 0 to 3 and y is 0 or 1. Of these hydrochloropropanes and hydrochlorofluoropropanes are more preferred. The most preferred hydrochloroalkanes and hydrochlorofluoroalkanes non-exclusively include $CCl_3CH_2CHCl_2$, $CFCl_2CH_2CHCl_2$, $CF_2ClCH_2CHCl_2$, $CF_3CH_2CHCl_2$, $CF_3CH_2CHFCl$, $CCl_3CH_2CHFCl$, $CFCl_2CH_2CHFCl$, $CF_2ClCH_2CHFCl$ and mixtures thereof. The process of the present invention is most particularly useful for fluorinating 1,1,1,3,3-pentachloropropane to 1,1,1,3,3-pentafluoropropane.

Suitable HCCs and HCFCs also include hydrochloroalkenes and hydrochlorofluoroalkenes having the formula $CF_xCl_{3-x}CH=CHY$ wherein x is 0 to 3 and Y is F or Cl. Of these, hydrochloropropenes and hydrochlorofluoropropenes are more preferred. The most preferred hydrochloroalkenes and hydrochlorofluoroalkenes non-exclusively include $CCl_3CH=CHF$, $CCl_3CH=CHCl$, $CFCl_2CH=CHF$, $CFCl_2CH=CHCl$, $CF_2ClCH=CHF$, $CF_2ClCH=CHCl$, $CF_3CH=CHF$, $CF_3CH=CHCl$, and mixtures thereof.

Many of the HCCs and HCFCs materials to be fluorinated in the present invention are not commercially available. However, they may be prepared by any one of the known methods reported in the art. See B. Boutevin, et al., Monofuinctional Vinyl Chloride Telomers. 1. Synthesis and Characterization of Vinyl Chloride Telomer Standards, 18 Eur. Polym. J. 675 (1982) in 97 Chemical Abstracts 182966c (1982); and Kotora, et al., Selective Additions of Polyhalogenated Compounds to Chloro Substituted Ethenes Catalyzed by a Copper Complex, 44(2) React.Kinet. Catal. Lett. 415 (1991). See also the method disclosed in Examples 1 and 2 of U.S. patent application Ser. No. 08/519,857, filed Aug. 25, 1995. All of the above patents, application and disclosures are incorporated herein by reference.

Suitable catalysts for use in the present invention include: (i) a pentavalent molybdenum halide of the formula $MoCl_{5-z}F_z$ wherein z is 0 to 5; (ii) a tetravalent tin halide of the formula $SnCl_{4-y}F_y$ wherein y is 0 to 4; (iii) a tetravalent titanium halide of the formula $TiCl_{4-x}F_x$ wherein x is 0 to 4; (iv) mixtures of a pentavalent tantalum halide of the formula $TaCl_{5-n}F_n$ wherein n is 0 to 5 with a tetravalent tin halide of the formula $SnCl_{4-y}F_y$ wherein y is 0 to 4; (v) mixtures of a pentavalent tantalum halide of the formula $TaCl_{5-n}F_n$ wherein n is 0 to 5 with a tetravalent titanium halide of the formula $TiCl_{4-x}F_x$ wherein x is 0 to 4; (vi) mixtures of a pentavalent niobium halide of the formula $NbCl_{5-m}F_m$ wherein m is 0 to 5 with a tetravalent tin halide of the formula $SnCl_{4-y}F_y$ wherein y is 0 to 4; (vii) mixtures of a pentavalent niobium halide of the formula $NbCl_{5-m}F_m$ wherein m is 0 to 5 with a tetravalent titanium halide of the formula $TiCl_{4-x}F_x$ wherein x is 0 to 4; (viii) mixtures of a pentavalent antimony halide of the formula $SbCl_{5-p}F_p$ wherein p is 0 to 5 with a tetravalent tin halide of the formula $SnCl_{4-y}F_y$ wherein y is 0 to 4; (ix) mixtures of a pentavalent antimony halide of the formula $SbCl_{5-p}F_p$ wherein p is 0 to 5 with a tetravalent titanium halide of the formula $TiCl_{4-x}F_x$ wherein x is 0 to 4; (x) mixtures of a pentavalent molybdenum halide of the formula $MoCl_{5-z}F_z$ wherein z is 0 to 5 with a tetravalent tin halide of the formula $SnCl_{4-y}F_y$ wherein y is 0 to 4; (xi) mixtures of a pentavalent molybdenum halide of the formula $MoCl_{5-z}F_z$ wherein z is 0 to 5 with a tetravalent titanium halide of the formula $TiCl_{4-x}F_x$ wherein x is 0 to 4 and (xii) mixtures of a pentavalent antimony halide of the formula $SbCl_{5-p}F_p$ wherein p is 0 to 5 with a trivalent antimony halide of the formula $SbCl_{3-p}F_p$ wherein p is 0 to 3.

In the preferred embodiment, for group (iv) through (xii) catalysts above, the molar ratios of the components of the mixtures typically range from about 1:9 to about 9:1, preferably from about 3:7 to about 7:3 and most preferably about 1:1. Of the above, the preferred catalysts are pentavalent molybdenum halides, a tetravalent tin halides, a tetravalent titanium halides, and mixtures of a pentavalent antimony halides or mixed halides with a trivalent antimony halides or mixed halides. The term "mixed halide" means more than one different halide is present in the compound. The most preferred catalysts are tin tetrahalide and mixtures of $TaCl_5$ and $SnCl_4$.

If in the course of conducting the inventive process the catalyst decreases in catalytic effectiveness, it can be regenerated. One method of regenerating the catalyst is to treat it by flowing a stream of an excess of gaseous chlorine over the catalyst for from about 1 to about 2 hours at a temperature of from about 65° C. to about 100° C.

Resulting fluorination products such as HFC-245fa may be recovered from the reaction mixture via any separation and purification method known in the art such as neutralization and distillation. The process may be carried out either in a batch or continuous method. In a continuous process, the HCC or HCFC compound to be fluorinated and HF are preferably fed simultaneously to the reactor after the reactor reaches the desired temperature. The temperature and pressure of the fluorination reaction remain the same for both the batch and continuous modes of operation. The residence time for a continuous process varies from about 1 second to about 2 hours, preferably from about 5 seconds to about 1 hour and most preferably from about 10 seconds to about 30 minutes. The catalyst concentration is not critical for a continuous process. A sufficient quantity of catalyst must be present to effect the fluorination in the residence times described above. The continuous method requires the removal of fluorination products and hydrogen chloride from the reactor continuously as it is formed. Unreacted HF and under-fluorinated materials such as $CFCl_2CH_2CHCl_2$; $CF_2ClCH_2CHCl_2$; $CF_3CH_2CHCl_2$; $CF_3CH_2CHFCl$, $CCl_3CH_2CHFCl$; $CFCl_2CH_2CHFCl$; $CF_2ClCH_2CHFCl$; $CF_3CH=CHF$, $CF_3CH=CHCl$; $CCl_3CH=CHF$; $CFCl_2CH=CHF$; $CFCl_2CH=CHCl$; $CF_2ClCH=CHF$ and $CF_2ClCH=CHCl$ may be recycled back to the same reactor or optionally to a separate reactor.

The following non-limiting examples serve to illustrate the invention.

EXAMPLE 1

Fluorination of $CCl_3CH_2CHCl_2$ with $HF/SnCl_4$

A 600 ml Monel autoclave equipped with a magnetic drive was charged with 9.4 g $SnCl_4$ and cooled to −20° C. The autoclave was then evacuated and charged with 60.5 g anhydrous HF. The contents were cooled to −25° C. and 54 g $CCl_3CH_2CHCl_2$ was added thereto. The autoclave was then connected to a packed column/condenser assembly, and the condenser was maintained at −5° C. The column/condenser assembly serves to vent off gaseous HCl and effect a HCl/HF separation. The reaction mixture was heated with stirring to about 135° C. over 2 hours and maintained at that temperature for an additional 3 hours. During this period, the pressure in the autoclave was maintained between 300–400 psig by periodically venting pressure in excess of 400 psig. Venting was done from the top of the condenser to an aqueous KOH scrubber which was connected to two −78° C. cold traps. The reactor was then completely vented to the cold traps to give 33.2 g of product. Gas chromatographic analysis of the product showed the presence of the following products with their relative area percentages: $CF_3CH_2CHF_2$ (57), $CF_3CH_2CHFCl$ (9), $CF_3CH=CHF$ (3), $CF_3CH=CHCl$ (30) and $C_6$ materials (1). Relative area percentages in these examples closely approximates weight percent.

EXAMPLE 2

Fluorination of $CCl_3CH_2CHCl_2$ with $HF/TiCl_4$

The experiment described in Example 1 was repeated except that $TiCl_4$ was used as the catalyst. To the apparatus described in Example 1 was charged 6.8 g $TiCl_4$, 63.1 g HF and 54 g $CCl_3CH_2CHCl_2$. This mixture was heated with stirring to about 135° C. in 2 hours and maintained at that temperature for an additional 3 hours. Venting the reactor completely to the cold traps gave 17.3 g of product. Gas chromatographic analysis of the product showed the presence of the following products with their relative area percentages: $CF_3CH_2CHF_2$ (25), $CF_3CH_2CHFCl$ (16), $CF_3CH=CHF$ (3), $CF_3CH=CHCl$ (55) and $C_6$ materials (1).

EXAMPLE 3

Fluorination of $CCl_3CH_2CHCl_2$ with $HF/MoCl_5$

The experiment described in Example 1 was repeated except that $MoCl_5$ was used as the catalyst. To the apparatus described in Example 1 was charged 10.0 g $MoCl_5$, 65.3 g HF and 54.1 g $CCl_3CH_2CHCl_2$. This mixture was heated with stirring to about 135° C. in 2 hours and maintained at that temperature for an additional 3 hours. Venting the reactor completely to the cold traps gave 15.0 g of product. Gas chromatographic analysis of the product showed the presence of the following products with their relative area percentages: $CF_3CH_2CHF_2$ (44), $CF_3CH_2CHFCl$ (15), $CF_3CH=CHF$ (3), $CF_3CH=CHCl$ (37) and $C_6$ materials (1).

EXAMPLE 4

Fluorination of $CCl_3CH_2CHCl_2$ with $HF/SbCl_5/SbCl_3$

The experiment described in Example 1 was repeated except that an equal molar mixture of $SbCl_5$ and $SbCl_3$ was used as the catalyst. To the apparatus described in Example 1 was charged 5.4 g $SbCl_5$, 4.1 g $SbCl_3$, 60.2 g HF and 54 g $CCl_3CH_2CHCl_2$. This mixture was heated with stirring to about 135° C. in 2 hours and maintained at that temperature for an additional 3 hours. Venting the reactor completely to the cold traps gave 26.8 g of product. Gas chromatographic analysis of the product showed the presence of the following products with their relative area percentages: $CF_3CH_2CHF_2$ (91), $CF_3CH_2CHFCl$ (5), $CF_3CH=CHF$ (1), $CF_3CH=CHCl$ (2) and $C_6$ materials (1).

EXAMPLE 5

Fluorination of $CCl_3CH_2CHCl_2$ with $HF/TaCl_5/SnCl_4$

The experiment described in Example 1 was repeated except that an equimolar mixture of $TaCl_5$ and $SnCl_4$ was used as the catalyst. To the apparatus described in Example 1 was charged 6.5 g of $TaCl_5$, 4.7 g $SnCl_4$, 64.0 g HF and 54 g $CCl_3CH_2CHCl_2$. This mixture was heated with stirring to about 126° C. in 2 hours and maintained at that temperature for an additional 3 hours. Venting the reactor completely to the cold traps gave 32.6 g of product. Gas chromatographic analysis of the product showed the presence of the following products with their relative area percentages: $CF_3CH_2CHF_2$ (91), $CF_3CH_2CHFCl$ (1.3), $CF_3CH=CHF$ (0.2), $CF_3CH=CHCl$ (7.1) and $C_6$ materials (0.4).

EXAMPLE 6

Fluorination of $CCl_3CH_2CHCl_2$ with $HF/SnCl_4$ at 125° C.

The experiment described in Example 1 was repeated except that the fluorination was conducted at 125° C. To the apparatus described in Example 1 was charged 9.4 g $SnCl_4$, 65.9 g HF and 54 g $CCl_3CH_2CHCl_2$. This mixture was heated with stirring to about 125° C. in 2 hours and maintained at that temperature for an additional 3 hours. Venting the reactor completely to the cold traps gave 23.8 g of product. Gas chromatographic analysis of the product showed the presence of the following products with their relative area percentages: $CF_3CH_2CHF_2$ (40), $CF_3CH_2CHFCl$ (19), $CF_3CH=CHF$ (3), $CF_3CH=CHCl$ (37) and $C_6$ materials (1).

EXAMPLE 7

Fluorination of $CF_3CH=CHF$ with $HF/SnCl_4$ at 115° C.

The experiment described in Example 1 was repeated except that $CF_3CH=CHF$ was used as the starting material. To the apparatus described in Example 1 was charged 18.8 g $SnCl_4$, 42.4 g HF and 57.4 g $CF_3CH=CHF$. This mixture was heated with stirring to about 115° C. in 2 hours and maintained at that temperature for an additional 3 hours. Venting the reactor completely to the cold traps gave 52.6 g of product. Gas chromatographic analysis of the product showed the presence of the following products with their relative area percentages: $CF_3CH_2CHF_2$ (39), $CF_3CH_2CHFCl$ (2), $CF_3CH=CHF$ (47), and $CF_3CH=CHCl$ (11).

EXAMPLE 8

Fluorination of $CF_3CH=CHF$ with $HF/SbCl_5$ at 93° C.

The experiment described in Example 1 was repeated except that $SbCl_5$ and $CF_3CH=CHF$ were used as the catalyst and the starting material. To the apparatus described in Example 1 was charged 21.6 g $SbCl_5$, 36.0 g HF and 59.2 g $CF_3CH=CHF$. This mixture was heated with stirring to about 93° C. in 2 hours and maintained at that temperature for an additional 3 hours. Venting the reactor completely to the cold traps gave 48.0 g of product. Gas chromatographic analysis of the product showed the presence of the following products with their relative area percentages: $CF_3CH_2CHF_2$ (90), $CF_3CH_2CHFCl$ (4), $CF_3CH=CHF$ (1), $CF_3CH=CHCl$ (3) and high boilers (2).

EXAMPLE 9

Fluorination of $CF_3CH=CHF$ with $HF/TaCl_5$ at 117° C.

The experiment described in Example 1 was repeated except that $TaCl_5$ and $CF_3CH=CHF$ were used as the catalyst and the starting material. To the apparatus described in Example 1 was charged 25.8 g $TaCl_5$, 36.8 g HF and 57.3 g $CF_3CH=CHF$. This mixture was heated with stirring to about 117° C. in 2 hours and maintained at that temperature for an additional 3 hours. Venting the reactor completely to the cold traps gave 48.3 g of product. Gas chromatographic analysis of the product showed the presence of the following products with their relative area percentages: $CF_3CH_2CHF_2$ (98), $CF_3CH=CHF$ (1), and $CF_3CH=CHCl$ (1).

EXAMPLE 10

Fluorination of $CF_3CH=CHCl$ with $HF/SbCl_5$ at 95° C.

The experiment described in Example 1 was repeated except that $SbCl_5$ and $CF_3CH=CHCl$ were used as the catalyst and the starting material. To the apparatus described in Example 1 was charged 22.4 g $SbCl_5$, 45.3 g HF and 75.2 g $CF_3CH=CHCl$. This mixture was heated with stirring to about 95° C. in 1 hour and maintained at that temperature for an additional 4 hours. Venting the reactor completely to the cold traps gave 72.9 g of product. Gas chromatographic analysis of the product showed the presence of the following products with their relative area percentages: $CF_3CH_2CHF_2$ (83), $CF_3CH_2CHFCl$ (5), $CF_3CH=CHF$ (1), $CF_3CH=CHCl$ (9), $CF_2ClCH_2CHCl_2$ (1) and $CCl_3CH_2CHCl_2$ (1).

EXAMPLE 11

Fluorination of $CF_3CH=CHCl$ with $HF/TaCl_5$ at 116° C.

The experiment described in Example 1 was repeated except that $TaCl_5$ and $CF_3CH=CHCl$ were used as the catalyst and the starting material. To the apparatus described in Example 1 was charged 26.9 g $TaCl_5$, 47.5 g HF and 76.4 g $CF_3CH—CHCl$. This mixture was heated with stirring to about 116° C. in 1 hour and maintained at that temperature for an additional 4 hours. Venting the reactor completely to the cold traps gave 79.5 g of product. Gas chromatographic analysis of the product showed the presence of the following products with their relative area percentages: $CF_3CH_2CHF_2$ (97), $CF_3CH_2CHFCl$ (1), $CF_3CH=CHF$ (traces), $CF_3CH=CHCl$ (1), and $CF_2ClCH_2CHCl_2$ (1).

What is claimed is:

1. Amended) A fluorinating process which comprises reacting at least one hydrochlorocarbon or hydrochlorofluorocarbon compound with hydrogen fluoride in the liquid phase and in the presence of at least one catalyst selected from the group consisting of (i) a pentavalent molybdenum halide of the formula $MoCl_{5-z}F_z$ wherein z is 0 to 5; (ii) a tetravalent tin halide of the formula $SnCl_{4-y}F_y$ wherein y is 0 to 4; (iii) a tetravalent titanium halide of the formula $TiCl_{4-x}F_x$ wherein x is 0 to 4; (iv) mixtures of a pentavalent tantalum halide of the formula $TaCl_{5-n}F_n$ wherein n is 0 to 5 with a tetravalent titanium halide of the formula $TiCl_{4-x}F_x$ wherein x is 0 to 4; (v) mixtures of a pentavalent niobium halide of the formula $NbCl_{5-m}F_m$ wherein m is 0 to 5 with a tetravalent tin halide of the formula $SnCl_{4-y}F_y$ wherein y is 0 to 4; (vi) mixtures of a pentavalent niobium halide of the formula $NbCl_{5-m}F_m$ wherein m is 0 to 5 with a tetravalent titanium halide of the formula $TiCl_{4-x}F_x$ wherein x is 0 to 4; (vii) mixtures of a pentavalent antimony halide of the formula $SbCl_{5-p}F_p$ wherein p is 0 to 5 with a tetravalent tin halide of the formula $SnCl_{4-x}F_x$ wherein x is 0 to 4; (viii) mixtures of a pentavalent antimony halide of the formula $SbCl_{5-p}F_p$ wherein p is 0 to 5 with a tetravalent titanium halide of the formula $TiCl_{4-x}F_x$ wherein x is 0 to 4; (ix) mixtures of a pentavalent molybdenum halide of the formula $MoCl_{5-z}F_z$ wherein z is 0 to 5 with a tetravalent tin halide of the formula $SnCl_{4-y}F_y$ wherein y is 0 to 4; (x) mixtures of a pentavalent molybdenum halide of the formula $MoCl_{5-z}F_z$ wherein z is 0 to 5 with a tetravalent titanium halide of the formula $TiCl_{4-x}F_x$ wherein x is 0 to 4 and (xi) mixtures of a pentavalent antimony halide of the formula $SbCl_{5-p}F_p$ wherein p is 0 to 5 with a trivalent antimony halide of the formula $SbCl_{3-p}F_p$ wherein p is 0 to 3.

2. The process of claim 1 wherein the hydrochlorocarbon or hydrochlorofluorocarbon compound is a hydrochloropropane or hydrochlorofluoropropane.

3. The process of claim 1 wherein the hydrochlorocarbon or hydrochlorofluorocarbon compound has the formula $CF_xCl_{3-x}CH_2CHF_yCl_{2-y}$, wherein x is 0 to 3 and y is 0 or 1.

4. The process of claim 1 wherein the hydrochlorocarbon or hydrochlorofluorocarbon compound is selected from the group consisting of $CCl_3CH_2CHCl_2$, $CFCl_2CH_2CHCl_2$, $CF_2ClCH_2CHCl_2$, $CF_3CH_2CHCl_2$, $CF_3CH_2CHFCl$, $CCl_3CH_2CHFCl$, $CFCl_2CH_2CHFCl$, $CF_2ClCH_2CHFCl$ and mixtures thereof.

5. The process of claim 1 wherein the hydrochlorocarbon or hydrochlorofluorocarbon compound is a hydrochloropropene or hydrochlorofluoropropene.

6. The process of claim 1 wherein the hydrochlorocarbon or hydrochlorofluorocarbon compound has the formula $CF_xCl_{3-x}CH\!\!=\!\!CHY$ wherein x is 0 to 3 and y is F or Cl.

7. The process of claim 1 wherein the hydrochlorocarbon or hydrochlorofluorocarbon compound is selected from the group consisting of $CCl_3CH\!\!=\!\!CHF$, $CCl_3CH\!\!=\!\!CHCl$, $CFCl_2CH\!\!=\!\!CHF$, $CFCl_2CH\!\!=\!\!CHCl$, $CF_2ClCH\!\!=\!\!CHF$, $CF_2ClCH\!\!=\!\!CHCl$, $CF_3CH\!\!=\!\!CHF$ and $CF_3CH\!\!=\!\!CHCl$.

8. The process of claim 1 wherein the hydrochlorocarbon comprises 1,1,1,3,3-pentachloropropane and the product of the fluorination process comprises 1,1,1,3,3-pentafluoropropane.

9. The process of claim 1 wherein the catalyst is selected from the group consisting of pentavalent molybdenum halides, a tetravalent tin halides, a tetravalent titanium halides, and mixtures of pentavalent antimony halides or mixed halides with trivalent antimony halides or mixed halides.

10. The process of claim 1 wherein the catalyst comprises a pentavalent molybdenum halide of the formula $MoCl_{5-z}F_z$ wherein z is 0 to 5.

11. The process of claim 1 wherein the catalyst comprises a tetravalent tin halide of the formula $SnCl_{4-y}F_y$ wherein y is 0 to 4.

12. The process of claim 1 wherein the catalyst comprises a tetravalent titanium halide of the formula $TiCl_{4-x}F_x$ wherein x is 0 to 4.

13. The process of claim 1 wherein the catalyst comprises mixtures of a pentavalent tantalum halide of the formula $TaCl_{5-n}F_n$ wherein n is 0 to 5 with a tetravalent titanium halide of the formula $TiCl_{4-x}F_x$ wherein x is 0 to 4.

14. The process of claim 1 wherein the catalyst comprises mixtures of a pentavalent niobium halide of the formula $NbCl_{5-m}F_m$ wherein m is 0 to 5 with a tetravalent tin halide of the formula $SnCl_{4-y}F_y$ wherein y is 0 to 4.

15. The process of claim 1 wherein the catalyst comprises mixtures of a pentavalent niobium halide of the formula $NbCl_{5-m}F_m$ wherein m is 0 to 5 with a tetravalent titanium halide of the formula $TiCl_{4-x}F_x$ wherein x is 0 to 4.

16. The process of claim 1 wherein the catalyst comprises mixtures of a pentavalent antimony halide of the formula $SbCl_{5-p}F_p$ wherein p is 0 to 5 with a tetravalent tin halide of the formula $SnCl_{4-y}F_y$ wherein y is 0 to 4.

17. The process of claim 1 wherein the catalyst comprises mixtures of a mixture of a pentavalent antimony halide of the formula $SbCl_{5-p}F_p$ wherein p is 0 to 5 with a tetravalent titanium halide of the formula $TiCl_{4-x}F_x$ wherein x is 0 to 4.

18. The process of claim 1 wherein the catalyst comprises mixtures of a pentavalent molybdenum halide of the formula $MoCl_{5-z}F_z$ wherein z is 0 to 5 with a tetravalent tin halide of the formula $SnCl_{4-y}F_y$ wherein y is 0 to 4.

19. The process of claim 1 wherein the catalyst comprises mixtures of a pentavalent molybdenum halide of the formula $MoCl_{5-z}F_z$ wherein z is 0 to 5 with a tetravalent titanium halide of the formula $TiCl_{4-x}F_x$ wherein x is 0 to 4.

20. The process of claim 1 wherein the catalyst comprises mixtures of a pentavalent antimony halide of the formula $SbCl_{5-p}F_p$ wherein p is 0 to 5 with a trivalent antimony halide of the formula $SbCl_{3-p}F_p$ wherein p is 0 to 3.

21. The process of claim 1 wherein the catalyst is present in an amount of from about 2% to about 80% based on the mole percent of hydrochlorocarbon or hydrochlorofluorocarbon.

22. The process of claim 1 wherein the catalyst is present in an amount of from about 5% to about 50% based on the mole percent of hydrochlorocarbon or hydrochlorofluorocarbon.

23. The process of claim 1 wherein the catalyst is present in an amount of from about 10% to about 20% based on the mole percent of hydrochlorocarbon or hydrochlorofluorocarbon.

24. The process of claim 1 wherein the reaction is conducted at a temperature of from about 50° C. to about 200° C.

25. The process of claim 1 wherein the reaction is conducted at a temperature of from about 90° C. to about 140° C.

26. The process of claim 1 wherein the reaction is conducted for from about 1 to about 25 hours.

27. The process of claim 1 wherein the reaction is conducted for from about 2 to about 8 hours.

28. The process of claim 1 wherein the mole ratio of hydrogen fluoride to hydrochlorocarbon or hydrochlorofluorocarbon ranges from about 1:1 to about 15:1.

29. The process of claim 1 wherein the mole ratio of hydrogen fluoride to hydrochlorocarbon or hydrochlorofluorocarbon ranges from about 6:1 to about 15:1.

30. The process of claim 1 wherein the reaction is conducted at a pressure of from about 50 psig to about 600 psig.

31. The process of claim 1 wherein the catalysts in the mixtures of groups (iv) through (xii) are present in a molar ratio of from about 1:9 to about 9:1.

32. The process of claim 1 wherein the process is conducted in a continuous mode and the residence time of the at least one hydrochlorocarbon or hydrochlorofluorocarbon compound with hydrogen fluoride in the presence of the at least one catalyst ranges from about 1 second to about 2 hours.

* * * * *